May 8, 1956 C. E. SULLIVAN Plant Pat. 1,476

WALNUT TREE

Filed March 22, 1955

WITNESS

Addison E. Avery

INVENTOR

Charles Edward Sullivan

Webster & Webster

ATTYS.

United States Patent Office

Plant Pat. 1,476

Patented May 8, 1956

1,476

WALNUT TREE

Charles Edward Sullivan, Yuba City, Calif.

Application March 22, 1955, Serial No. 496,089

1 Claim. (Cl. 47—62)

This invention relates to a new and distinct variety of walnut tree which was originated by me as a seedling of a cross of the Payne walnut as the seed parent and the Bijou walnut as the pollen parent.

A substantial number of selected nuts from such cross were planted by me on my ranch near Yuba City, county of Sutter, State of California, and of the resulting seedlings a particular one thereof—which is the instant variety—evidenced, when it came into bearing, certain very desirable characteristics for commercial growing.

I therefore selected the variety for reproduction; asexual reproduction having been accomplished by me on my ranch located as aforesaid by patch-budding the variety to an orchard row of Paradox Hybrid seedlings. When these asexual reproductions came into bearing they were found to carry forward all of the characteristics of the original and parent seedling.

The new and distinctive characteristics of the present variety of walnut will be evident from the following:

The nut produced by this variety is of spectacularly large size and extremely well filled, especially for a large nut; the meat consistently being of excellent quality, with a relatively high percentage of meat to shell by weight.

Additionally, the present variety is a prolific as well as an early bearer, having produced—from a single tree—twenty-seven pounds of nuts in the fifth year of growth.

Further, the nut of the present variety is relatively free from blight and sunburn, particularly for a variety which is an early bearer.

As compared to the Payne walnut the present variety leafs out later in the spring and harvests in the late summer at substantially the same time, and the nut is at least twice the size and of better market quality.

None of the mentioned previously existent varieties of walnuts are patented.

Figure 1:
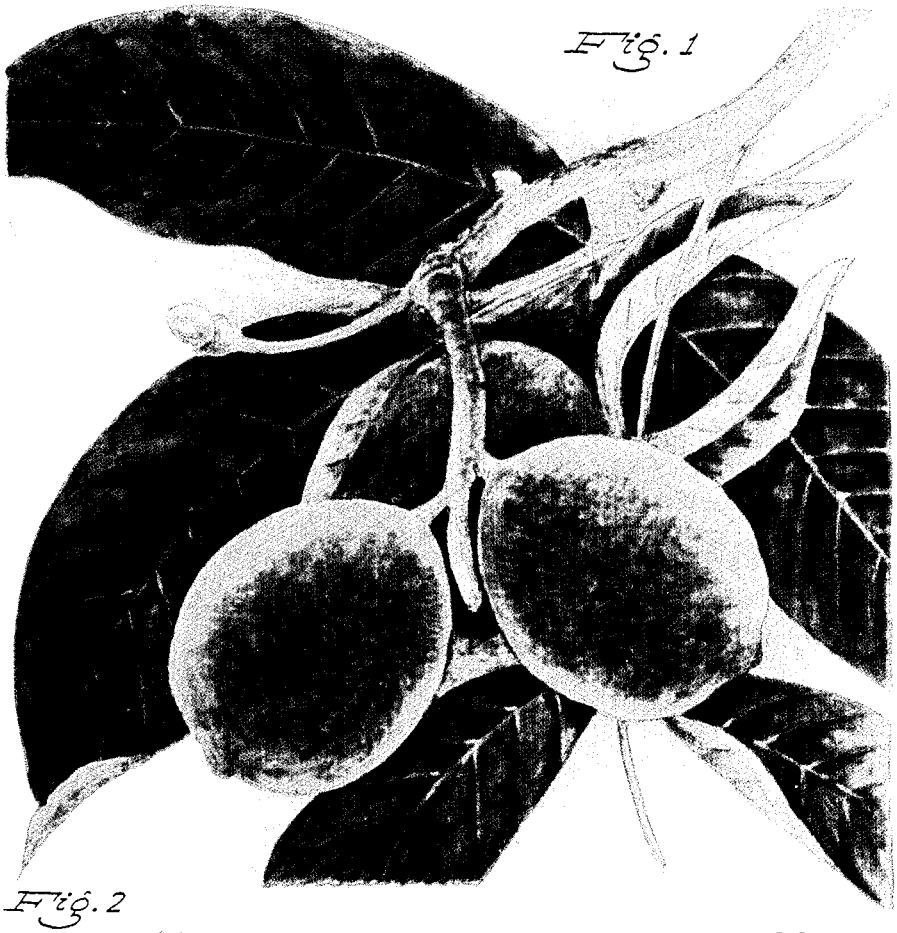
Fig. 1 is an elevation showing a cluster of the walnuts, together with twigs and leaves.
Figure 2:
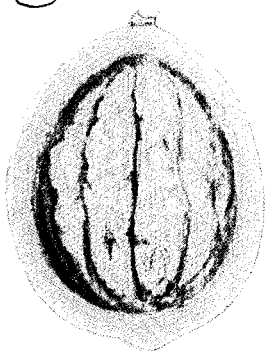
Fig. 2 is an elevation of one of the nuts in the hull; the latter being half cut away.
Figure 4:
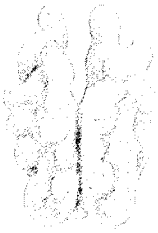
Fig. 4 is an elevation of the kernal removed from the shell.
Figure 3:
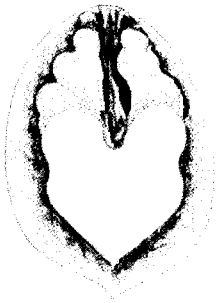
Fig. 3 is an elevation of one-half of a shell with the corresponding portion of the kernal remaining therein.

Referring now more specifically to the botanical details of this new and distinct variety of walnut tree, the following is an outline description thereof; all major color plate identifications being by reference to Maerz and Paul Dictionary of Color:

Tree:

*Growing habit.*—Lateral growing habit similar to Payne walnut.

*Adaptability.*—Adaptable to the common types of soil in which walnuts thrive.

*Productivity.*—Early bearer. Highly prolific. Substantial production by the fifth year of growth.

Trunk: Light colored; slightly rough; strong; vigorous.

Branches: Central leaders upright. Light at trunk, turning to dark brown in outer limbs. Light speckle.

*Twigs.*—On laterals throughout tree; long; profuse.

Foliage: Fairly heavy.

Disease resistance: Resistant to blight and sunburn to a much greater degree than Payne. The greater resistance to blight is by reason of leafing out later in the spring, and when not as subject to wet weather. The greater resistance to sunburn is due to the fact that the nuts of the present variety are well shaded by foliage, whereas on the Payne variety the nuts are not as shaded and thus are subject to more direct exposure to sunlight. These characteristics were ascertained by observing a tree of the present variety growing in an orchard block along with trees of the Payne variety; all of the trees having been of the same age and subject to the same conditions of culture, irrigation, fertilization, and climate. In addition to such observation, crack tests of the crops have clearly established that the instant variety is less susceptible to blight and sunburn than the Payne.

Buds: Hardy; medium size; long; plump; numerous double.

Form: Central leaders and tops grow upright and vigorous. Lower limbs tend to grow laterally and droop, giving the lower part of the tree a squatty shape.

Leaves:

*Form.*—Lanceolate; acutely pointed.

*Margin.*—Even and smooth, with few indentations—sometimes light yellow.

*Petiole.*—Very short to substantially non-existent; strong; stiff.

*Color.*—Top side—medium to light green (22–L–7). Under side—lighter green (21–K–6). Pronounced yellow veins (20–K–1).

Nuts:

*Quality.*—Exceptionally good for an early bearing variety.

*Maturity.*—Harvests in late summer (September) at substantially the same time as the Payne walnut.

*Tenacity.*—Tenacious to twigs until hulls split, then fall readily by shaking.

*Cluster.*—Substantially all nuts in pairs or clusters of three; some clusters of four.

*Size.*—Exceptionally large, at least twice as large as the Payne walnut, and larger than the Bijou walnut. Averages 5¾″ circumferentially in an axial plane and 5″ circumferentially in a transverse plane.

*Weight.*—Well filled with meat, producing a heavy nut. Average 47% meat to shell by weight.

*Base.*—Flat; small, with pronounced corners.

*Point.*—Broad top, rounded slightly from fairly straight sides tilted slightly outward, coming to point at apex.

*Shell.*—Heavy; well sealed; handles well. Color.—Light brown (13–F–5), shading to darker brown (7–A–11).

*Hull.*—Medium thickness. Covers nut well. Many nuts fall free from hull before shaking. Outside color.—Light green (21–L–5), shading to darker green (22–L–7), somewhat mottled or spotted yellowish green (20–J–4). Flesh color.—Light yellowish green (19–L–2).

*Kernel or meat.*—Flavor—Exceptionally good for a large and early nut. Shape—Wing shaped. Outside color—Very light tan or golden (12–I–7, shading to 13–L–9), clear of speckles and spots. Flesh color—Ivory (9–B–1).

*Size.*—Extremely large. Substantially filling shell; cracks-out easily with a large percentage remaining whole.

The tree and its nuts herein described may vary in slight detail due to climatic and soil conditions under which the variety may be grown.

Having thus described my invention, I claim:

A new and distinct variety of walnut tree, substantially as illustrated and described, characterized by being an early, prolific bearer of particularly large size, extremely well filled nuts of consistently excellent quality which have a relatively high percentage of meat to shell by weight, and being relatively free from blight and sunburn; and further characterized—in comparison to the Payne walnut—by leafing out later in the spring, and harvesting in late summer at substantially the same time but bearing nuts which are at least twice the size, and of better quality.

No references cited.